(12) United States Patent
Ostuni

(10) Patent No.: US 11,648,488 B2
(45) Date of Patent: May 16, 2023

(54) METHOD OF REVAMPING OF A PLANT FOR DISTILLATION OF METHANOL

(71) Applicant: Casale SA, Lugano (CH)

(72) Inventor: Raffaele Ostuni, Lugano (CH)

(73) Assignee: Casale SA, Lugano (CH)

( * ) Notice: Subject to any disclaimer, the term of this patent is extended or adjusted under 35 U.S.C. 154(b) by 93 days.

(21) Appl. No.: 16/972,650

(22) PCT Filed: Apr. 10, 2019

(86) PCT No.: PCT/EP2019/059037
§ 371 (c)(1),
(2) Date: Dec. 7, 2020

(87) PCT Pub. No.: WO2019/233657
PCT Pub. Date: Dec. 12, 2019

(65) Prior Publication Data
US 2021/0252422 A1    Aug. 19, 2021

(30) Foreign Application Priority Data

Jun. 8, 2018    (EP) ..................................... 18176678

(51) Int. Cl.
*B01D 3/00* (2006.01)
*B01D 3/14* (2006.01)
(Continued)

(52) U.S. Cl.
CPC ............. *B01D 3/143* (2013.01); *B01D 3/007* (2013.01); *B01D 3/322* (2013.01); *C07C 29/84* (2013.01)

(58) Field of Classification Search
CPC ........ B01D 3/007; B01D 3/143; B01D 3/322; C07C 29/80; C07C 29/84; C07C 31/04
See application file for complete search history.

(56) References Cited

U.S. PATENT DOCUMENTS

| 4,013,521 A | 3/1977 | Scott |
| 4,210,495 A | 7/1980 | Pinto |

(Continued)

FOREIGN PATENT DOCUMENTS

| RU | 2512107 C2 | 4/2014 |
| SU | 618364 A1 | 8/1978 |

OTHER PUBLICATIONS

International Preliminary Report on Patentability dated Dec. 8, 2020, issued in connection with PCT/EP2019/059037.

(Continued)

*Primary Examiner* — Prem C Singh
*Assistant Examiner* — Brandi M Doyle
(74) *Attorney, Agent, or Firm* — Akerman LLP

(57) ABSTRACT

Method for revamping a refining section of a methanol distillation plant comprising a medium pressure (MP) column a low pressure (LP) column, wherein both said columns comprise at least one bottom boiler, a gaseous stream of distilled methanol withdrawn from the MP column is fed to at least one bottom boiler of the LP column and a liquid solution containing methanol withdrawn from the MP column is fed to the LP column, the method of revamping comprising the installation of a high pressure (HP) column; the installation of a line feeding a gaseous stream of distilled methanol from the HP column to at least one bottom boiler of the MP column and the installation of a bottom line for exporting from the HP column a liquid stream consisting essentially of water.

19 Claims, 2 Drawing Sheets

(51) Int. Cl.
*B01D 3/32* (2006.01)
*C07C 29/84* (2006.01)

(56) References Cited

U.S. PATENT DOCUMENTS

2015/0008116 A1  1/2015  Filippi et al.
2015/0202546 A1  7/2015  Filippi et al.

OTHER PUBLICATIONS

Written Opinion of the International Searching Authority issued in connection with PCT/EP2019/059037.
International Search Report issued in connection with PCT/EP2019/059037.

METHOD OF REVAMPING OF A PLANT FOR DISTILLATION OF METHANOL

CROSS-REFERENCE TO RELATED APPLICATIONS

This application is a national phase of PCT/EP2019/059037, filed Apr. 10, 2019, and claims priority to EP 18176678.3, filed Jun. 8, 2018, the entire contents of both of which are hereby incorporated by reference.

FIELD OF APPLICATION

The present invention relates to a method of revamping of a plant for distillation of methanol.

PRIOR ART

A methanol plant produces an aqueous solution of methanol containing reaction by-products such as ethanol and higher alcohols (e.g. propanol), ketones (e.g. acetone), aldehydes, and dissolved gases mainly including $H_2$, $CO$, $CO_2$, $N_2$, $CH_4$. This aqueous solution is termed crude methanol.

Crude methanol is distilled to meet the purity specification required on the market. For example, the specification grade AA requires a minimum methanol concentration of 99.85% by weight and requires that ethanol is not more than 10 ppm by weight.

Distillation is performed in a refining section which comprises one or more refining columns. Generally, a refining column separates one or more light products (i.e. having a relatively low boiling temperature, e.g. methanol) at the top from one or more heavy products (i.e. having a relatively high boiling temperature, e.g. water) at the bottom.

A typical refining section includes two refining columns, namely a medium pressure (MP) column and a low pressure (LP) column, respectively, operating at a medium pressure (e.g. around 7-10 bar) and at a low pressure (e.g. around 2 bar).

The MP column has a steam heated reboiler and an overhead condenser. The MP delivers an overhead stream of distilled methanol which is condensed in the overhead condenser, and a bottom liquid stream containing water and methanol, which is supplied to the LP column for further refining.

The overhead condenser of the MP column is the reboiler of the LP column. The LP column delivers an overhead stream of distilled methanol, a bottom liquid stream consisting essentially of water, and one or more side streams collectively denoted as "fusel oil" mainly containing water, residual methanol and reaction by-products of the synthesis reaction having intermediate boiling points between methanol and water, for example higher alcohols. The flow rate of the fusel oil and the tray from which it is withdrawn are selected to meet the required specification for methanol top product as regards the content of ethanol and other impurities. Said fusel oil has a certain heat value and is commonly used as a fuel.

Said refining section may also include a preliminary treatment or topping column for the separation of volatile compounds (e.g. $H_2$, $CO$, $CO_2$, $N_2$, $CH_4$, acetone) from the crude methanol. Said column operates substantially at atmospheric pressure or slightly higher pressure (e.g. 1.5 bar).

A configuration with a topping column and two distillation columns is disclosed in U.S. Pat. No. 4,210,495.

In recent years, the need of increasing the production capacity (i.e. the amount of methanol produced) without excessive capital cost has been strongly felt. However, the existing refining section with a MP column and a LP column do not provide room for a significant capacity increase.

SUMMARY OF THE INVENTION

The purpose of the present invention is to increase the capacity of a refining section of a methanol distillation plant comprising a MP distillation column and a LP distillation column, while maintaining a low energy consumption and low capital costs and without overloading the existing MP and LP distillation sections.

These aims are reached with a method for revamping a refining section according to claim 1. Preferred features of the method are stated in the dependent claims.

The invention provides a method for revamping a refining section fed with a stream of crude methanol and comprising a medium pressure (MP) refining column arranged to operate at a first distillation pressure (p1) and a low pressure (LP) refining column arranged to operate at a second distillation pressure (p2), wherein p1 is higher than p2 and wherein:

said MP refining column and said LP refining column each comprises at least one bottom boiler providing distillation heat to the MP column and the LP column, respectively, said MP refining column comprises a top outlet line for a gaseous stream of distilled methanol and a bottom outlet line for a solution containing methanol, said top outlet line being directed to at least one bottom boiler of the LP refining column, wherein said gaseous stream of distilled methanol acts as a heat source, and said bottom outlet line being directed to the LP refining column, wherein said solution containing methanol is further refined, the method being characterized by:

installation of a high pressure (HP) refining column arranged to operate at a third distillation pressure (p3), wherein p3 is higher than p1;

installation of a line feeding a gaseous stream of distilled methanol withdrawn from the top of said HP column to at least one bottom boiler of the MP column, wherein said gaseous stream of distilled methanol acts as a heat source, and installation of a bottom outlet line for exporting a liquid stream consisting essentially of water from the newly installed HP column.

According to a preferred embodiment, said method of revamping also comprises the installation of at least one side outlet line for exporting a fusel oil from the newly installed HP column. A related advantage is a greater purity of methanol leaving the top of the HP column for a given composition of the crude methanol and for a given number of distillation stages.

The term "exporting" means that the liquid stream consisting essentially of water and the fusel oil, respectively, are not sent to any apparatus forming the refining section; on the contrary, they are exported as products from the refining section itself. Accordingly, said liquid stream consisting essentially of water is not fed to the existing refining columns, thus resulting in a maximization of the heat recovery with the gaseous stream withdrawn from the top of the HP column and in a debottlenecking of the refining section.

According to a preferred embodiment, said method of revamping further comprises the installation of at least one bottom boiler arranged to provide distillation heat to the MP refining column and the gaseous stream of distilled methanol withdrawn from the top of said HP column is advantageously fed to said newly installed bottom boiler or, in case of more than one bottom boiler, to at least one of them. Said bottom boiler(s) may be installed in place of the existing one(s) or arranged in series thereto.

The gaseous streams of distilled methanol withdrawn from the top of the HP and MP columns mainly consist of methanol with a low content of impurities according to the required specification (e.g. grade AA).

Therefore, the revamped refining section comprises at least three refining columns operating at three distillation pressure levels, namely the HP, MP and LP refining columns respectively operating at pressure p3, p1 and p2, wherein p3>p1>p2. The high distillation pressure (p3) is preferably 10-35 bar, for example at least 20 bar according to a specific implementation.

The newly installed HP column requires a heat source with a high energy level, for example steam condensing at a pressure of 10 bar or higher. Accordingly, the present method of revamping advantageously also comprises the installation of at least one boiler arranged to provide the distillation heat to said newly installed HP refining column.

The applicant has found that the installation of a HP refining column increases the possibilities of heat recovery inside the distillation process, thanks to the availability of a gaseous stream of distilled methanol at high temperature and high pressure. It has been found that the improved heat recovery over-compensates for the need of a heat input at a higher energy level.

Preferably, the gaseous stream of distilled methanol extracted from the HP column supplies heat to the MP column by indirect heat exchange with a solution containing methanol leaving the MP column. Said solution is for example taken from the bottom of the MP column and the heated solution is again fed to the bottom of said column, thus heating the MP column itself. Said solution is preferably at least partially evaporated by means of the effect of said heat exchange and said gaseous stream is preferably at least partially condensed during said heat exchange, obtaining a liquid stream of distilled methanol.

According to a preferred embodiment, the present method of revamping comprises the installation of a flow line returning part of said condensed liquid stream to the HP column, and the installation of a flow line for exporting a remaining part of said liquid stream from the refining section.

Similarly, the gaseous stream of distilled methanol extracted from the MP column supplies heat to the LP column preferably by indirect heat exchange with a solution containing methanol leaving the LP column which is preferably at least partially evaporated, and said gaseous stream is at least partially condensed into a liquid stream of distilled methanol.

Therefore, each of said gaseous streams of distilled methanol supplies distillation heat to the subsequent column, i.e. to the MP column and the LP column, by means of indirect heat exchange with a respective liquid solution containing methanol extracted from the MP and LP column, respectively. More preferably, the gaseous stream of distilled methanol condenses while the liquid solution evaporates. The condensation and evaporation, respectively, are at least partial and preferably they are total.

According to a preferred embodiment, the existing refining section also comprises a topping column arranged to remove the more volatile components and to operate at a topping pressure ($p_T$), wherein $p_T$ is not greater than p2. Said topping column comprises an inlet line for said crude methanol, a top outlet line for a gaseous stream of volatile components and a bottom outlet line for a liquid solution which is directed to the MP refining column, and the method of revamping according to the invention is characterized by the installation of a branch directing part of said liquid solution to the newly installed HP refining column.

Said topping pressure ($p_T$) is preferably close to atmospheric pressure, more preferably of about 1-1.5 bar.

According to an embodiment of the invention, the distillation pressure (p2) at which the LP column is operated is substantially greater than said topping pressure ($p_T$), the topping column comprises a bottom boiler, the LP column comprises a top outlet line for a gaseous stream of distilled methanol, and the method of revamping is characterized by the installation of a branch directing part of said gaseous stream of distilled methanol to the bottom boiler of the topping column, said part of the gaseous stream thus acting as a heat source for said boiler.

Said part of the gaseous stream extracted from the LP column is preferably at least partially condensed in the bottom boiler of the topping column by indirect heat exchange with a solution containing methanol leaving the bottom of the topping column, and said solution is preferably at least partially evaporated.

The LP column is the last column of the refining section. It is also denoted as bottoming column and p2 is also denoted as bottoming pressure.

The adoption of a bottoming pressure substantially higher than the topping pressure allows an energy saving and an optimisation of the flows of heat, using gaseous methanol distilled in the bottoming column to supply heat to the topping column.

The LP column typically also produces a bottom solution mainly consisting of water and at least one side stream of fusel oil.

Preferably, an embodiment of the invention with recovery of heat also from the bottoming column has the following pressures: topping pressure ($p_T$) of about 1.5 bar; pressure p3 of the HP column of about 30 bar; pressure p1 of the MP column of about 15-20 bar; pressure p2 of the LP column of at least 2 bar and preferably about 5 bar.

Preferably, an embodiment of the invention without recovery of heat from the bottoming column has the following pressures: topping pressure ($p_T$) and pressure p2 of the LP column of about 1.5 bar; pressure p3 of the HP column of about 18-20 bar; pressure p1 of the MP column of about 8-10 bar.

The method of revamping according to the present invention allows to obtain the energy advantage of heat integration by using the condensation heat of the gaseous stream of distilled methanol withdrawn from the newly installed HP column as distillation heat of the existing MP column.

Said method of revamping is particularly advantageous because the newly installed column allows to increase the capacity of the refining section while keeping a low steam consumption and without impacting the existing MP and LP columns. Indeed, the invention provides for less liquid feed to be treated in the existing MP and LP columns, because the newly installed HP column already delivers a bottom stream consisting essentially of water and preferably also one or more side streams of fusel oil. At the same time, the installation of the HP column and of the bottom line for exporting the liquid stream consisting essentially of water has the advantage of maximising the heat recovery.

DETAILED DESCRIPTION OF A PREFERRED EMBODIMENT

Figure 1:
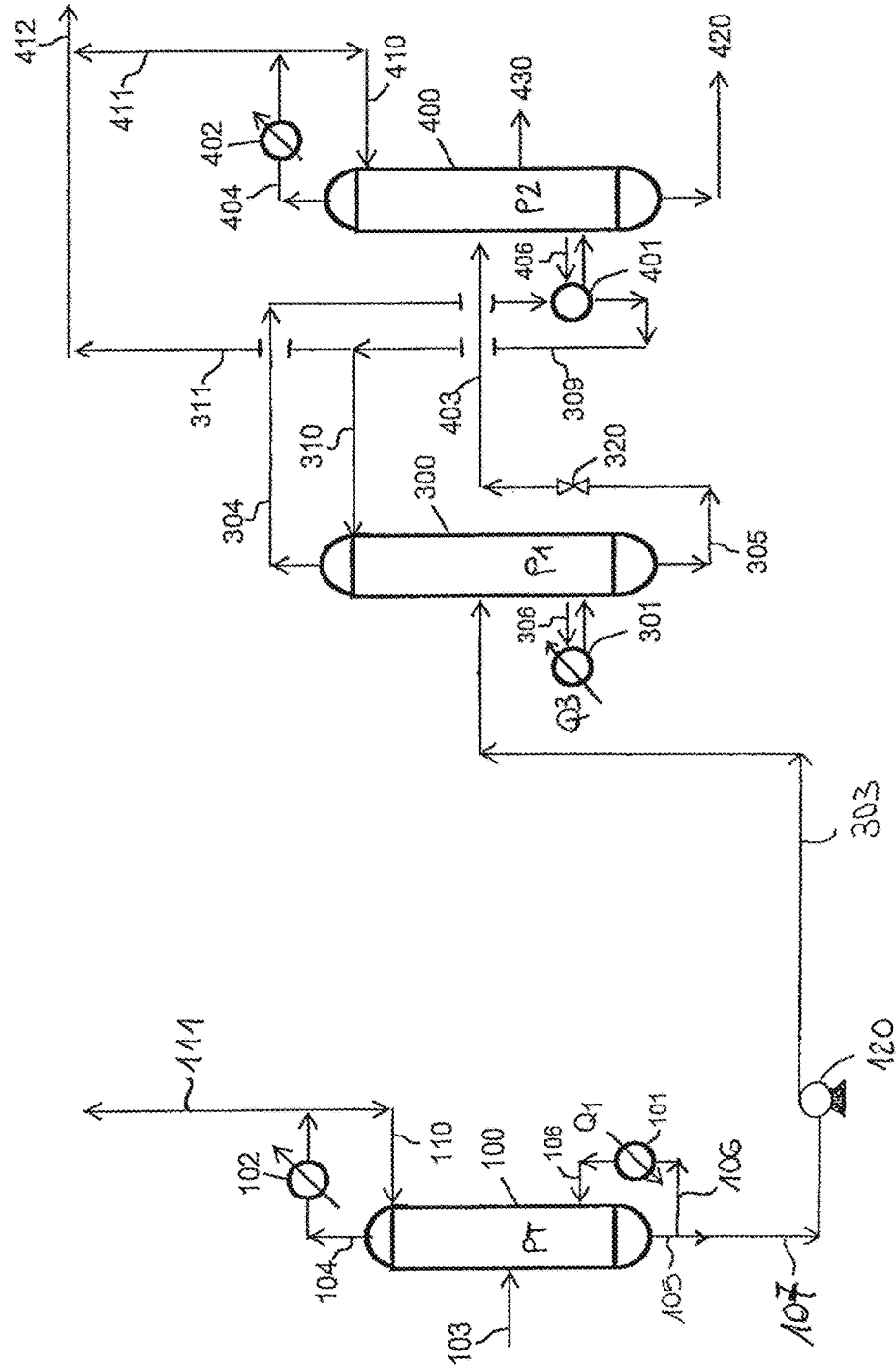
FIG. 1 is a diagram of a refining section of a methanol distillation plant according to the prior art.

The refining section of FIG. 1 comprises a topping column 100 and two distillation columns 300, 400. The distillation column 300 operates at pressure p1 and the distillation column 400 operates at pressure p2, wherein p1>p2. The topping column 100 operates at a pressure $p_T$ of about 1.5 bar; the pressure p2 of the column 400, in this example, is substantially equal to the topping pressure $p_T$, i.e. $p2=\sim p_T$.

The topping column 100 comprises a bottom reboiler 101 and a top condenser 102. The columns 300, 400 comprise respective bottom reboilers 301, 401. The bottom reboiler 401 of the column 400 also operates as a top condenser of the column 300, and the column 400 is provided with a top condenser 402.

The topping column 100 receives a flow of crude methanol 103 and separates a gaseous stream 104 containing volatile components lighter than methanol (light ends) and a bottom solution 105 containing methanol.

A first portion 106 of the bottom solution 105 is heated, preferably at least partially evaporated, and recirculated into the column 100 through the bottom reboiler 101. In an equivalent embodiment, instead of separating said portion 106, a liquid stream is taken from the bottom of the column 100, heated in the respective reboiler 101 and recirculated into the column 100. The reboiler 101 is fed by an external heat source Q1, for example steam.

A second portion 107 of the bottom solution is fed to a pump 120 that feeds the column 300 with a stream of methanol solution 303. The stream 303 is substantially at the pressure p1, apart from the pressure drop in the supply duct to the column 300.

The gaseous stream 104 is condensed in the top condenser 102 and a portion 110 of the condensed stream is recirculated into the column 100. The remaining portion 111 is discharged or removed.

The column 300 separates a gaseous stream 304 of distilled methanol at the pressure p1 and a bottom solution 305.

The bottom solution 305 passes through a throttling valve 320 or equivalent, obtaining a stream 403 substantially at the pressure p2. Said stream 403 feeds the subsequent LP column 400.

A liquid stream 306 is taken from the bottom of the column 300, heated in the respective reboiler 301 and recirculated into the column 300, thus heating the bottom of the column and maintaining the distillation process. In an equivalent embodiment, the liquid stream 306 is a portion of the bottom solution 305. The reboiler 301 is fed by an external heat source Q3, for example steam.

The gaseous stream 304 is used in the process to heat the column 400. Said stream 304 is fed to the hot side of the reboiler 401, wherein it is at least partially condensed providing a stream of condensed methanol 309. A portion 310 of said condensate 309 is recirculated in the column 300 and the remaining portion 311 is exported from the process as distilled methanol. Said reboiler 401 also operates as a top condenser of the column 300 since it condenses at least part of the distilled methanol 304, forming the top recirculation stream 310. Hence, said reboiler 401 is also termed reboiler/condenser.

The column 400 separates a further stream 404 of gaseous methanol, which is condensed in the top condenser 402 providing a condensed stream. A portion 410 of said condensed stream is reintroduced into the column 400 and the remaining portion 411 is discharged or removed.

Said LP column 400 also produces a stream 420 essentially consisting of water and a side stream 430 of fusel oil.

A liquid stream 406 is taken from the bottom of the column 400, subjected to heat exchange with the stream of gaseous methanol 304 in the reboiler 401, at least partially evaporated and recirculated into the column 400 to maintain the distillation process.

The streams 311, 411 are joined together to form the overall flow 412 of distilled methanol with a required purity grade (for example AA).

Figure 2:
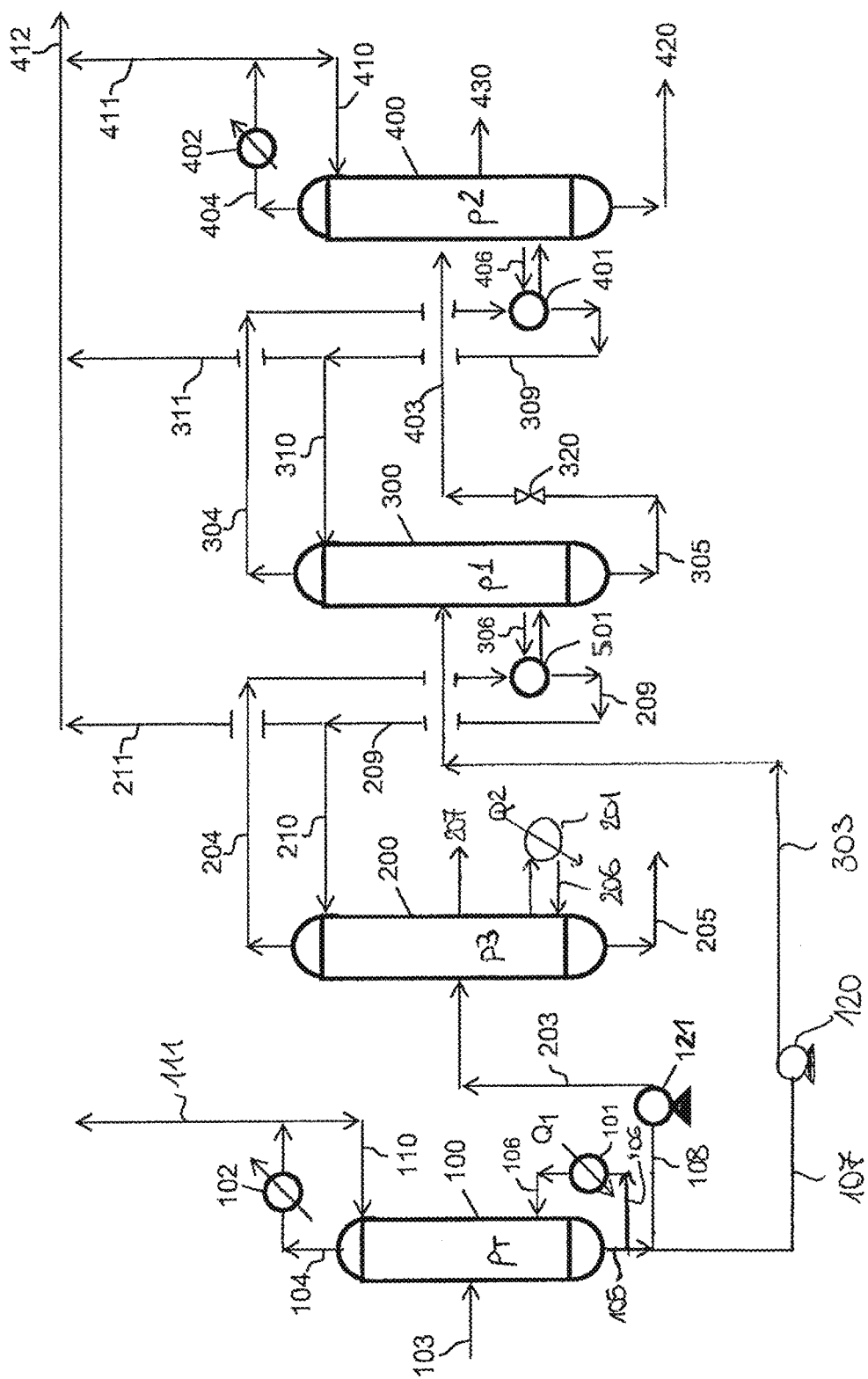
FIG. 2 is a diagram of the refining section of FIG. 1 after a revamping in accordance with an embodiment of the invention.

The prior art refining section shown in FIG. 1 is advantageously revamped to provide the refining section illustrated in FIG. 2, by means of the following operations:

installation of a refining column 200 arranged to operate at a pressure p3 higher than the pressure p1;

installation of a branch 108 directing part of the bottom solution leaving the topping column 100 to the newly installed HP column 200;

installation of a pump 121 for said branch 108;

installation of a bottom reboiler 501 in place of the bottom reboiler 301 of the MP refining column;

installation of a line 204 feeding a gaseous stream of distilled methanol withdrawn from the top of the newly installed column 200 to the bottom boiler 501, wherein said gaseous stream of distilled methanol acts as a heat source;

installation of a bottom outlet line 205 for exporting as a product a liquid stream consisting essentially of water from the newly installed column 200;

installation of a side outlet line 207 for exporting as a product a fusel oil from the newly installed HP column;

installation of a bottom boiler 201;

installation of a steam line Q2 and of a line 206 for extracting a liquid solution from the bottom of the column 200, said steam line Q2 and said line 206 feeding said newly installed boiler 201 to provide the distillation heat to the column 200.

The gaseous stream fed to the bottom boiler 501 through the newly installed line 204 is used to heat the column 300. Said gaseous stream is fed to the hot side of the reboiler 501, wherein it is at least partially condensed, and the liquid stream 306 taken from the bottom of the column 300 is fed to the cold side thereof, wherein it is at least part evaporated. The method of revamping comprises the installation of a line 209 for exporting the condensed methanol from the boiler 501, a line 210 for recirculating part of the condensed methanol in the column 200 and a line 211 for exporting the remaining part of the condensed methanol as a product.

The streams 211, 311, 411 are joined together to form the overall flow 412 of distilled methanol with a required purity grade (for example AA).

What is claimed is:

1. A method for revamping a refining section of a methanol distillation plant, said refining section receiving a stream of crude methanol and comprising a medium pressure (MP) refining column arranged to operate at a first distillation pressure (p1) and a low pressure (LP) refining column arranged to operate at a second distillation pressure (p2), wherein p1 is higher than p2 and wherein:

said MP refining column and said LP refining column each comprises at least one bottom boiler providing distillation heat to the MP column and the LP column, respectively, said MP refining column comprises a top outlet line for a gaseous stream of distilled methanol and a bottom outlet line for a solution containing methanol, said top outlet line being directed to at least one bottom boiler of the LP refining column, wherein said gaseous stream of distilled methanol acts as a heat source, and said bottom outlet line being directed to the LP refining column, wherein said solution containing methanol is further refined, the method comprising:

installation of a high pressure (HP) refining column arranged to operate at a third distillation pressure (p3), wherein p3 is higher than p1;

installation of a line feeding a gaseous stream of distilled methanol withdrawn from the top of said HP column to at least one bottom boiler of the MP column, wherein said gaseous stream of distilled methanol acts as a heat source, and installation of a bottom outlet line for exporting a liquid stream consisting essentially of water from the newly installed HP column.

2. The method according to claim 1, comprising the installation of at least one side outlet line for exporting a fusel oil from the newly installed HP column.

3. The method according to claim 1, comprising the installation of at least one bottom boiler arranged to provide distillation heat to the MP refining column and the line feeding said gaseous stream of distilled methanol withdrawn from the top of said HP column is directed to said newly installed bottom boiler or at least one of said newly installed bottom boilers.

4. The method according to claim 1, comprising the installation of at least one boiler arranged to provide the distillation heat to said newly installed HP refining column.

5. The method according to claim 1, wherein the gaseous stream of distilled methanol from the HP column supplies heat to the MP column by indirect heat exchange with a solution containing methanol leaving the MP column.

6. The method according to claim 5, wherein said gaseous stream of distilled methanol from the HP column is at least partially condensed during said heat exchange, obtaining a liquid stream of distilled methanol.

7. The method according to claim 6, characterised by installation of a flow line returning a part of said liquid stream of distilled methanol to the HP column and of a flow line for exporting a remaining part of said liquid stream of distilled methanol.

8. The method according to claim 1, wherein the existing refining section comprises a topping column arranged to operate at a topping pressure (pT) and said topping column comprises an inlet line for said crude methanol, a top outlet line for a gaseous stream of volatile components and a bottom outlet line for a liquid solution which is directed to the MP refining column, wherein said topping pressure (pT) is not greater than said second pressure (p2), said method comprising:

installation of a branch directing part of said liquid solution to the newly installed HP refining column.

9. The method according to claim 8, wherein the topping pressure (pT) is roughly equal to atmospheric.

10. The method according to claim 8, wherein said second distillation pressure (p2) is greater than said topping pressure (pT), said topping column comprises a bottom boiler and said LP column comprises a top outlet line for a gaseous stream of distilled methanol, said method comprising:

installation of a branch directing part of said gaseous stream of distilled methanol to the bottom boiler of the topping column, wherein said part of the gaseous stream acts as a heat source for said boiler.

11. The method according to claim 10, wherein said part of the gaseous stream of distilled methanol is at least partially condensed through indirect heat exchange with a solution containing methanol withdrawn from the topping column.

12. The method according to claim 10, wherein the second distillation pressure (p2) is at least 2 bar.

13. The method according to claim 12, wherein the third distillation pressure (p3) is about 30 bar and the first distillation pressure (p1) is about 15-20 bar.

14. The method according to claim 9, wherein the second distillation pressure (p2) is roughly equal to the topping pressure.

15. The method according to claim 14, wherein the third distillation pressure (p3) is about 20 bar and the first distillation pressure (p1) is about 8-10 bar.

16. The method according to claim 8, wherein the topping pressure (pT) is about 1.5 bar.

17. The method according to claim 11, wherein said solution is at least partially evaporated through the effect of said heat exchange.

18. The method according to claim 12, wherein the second distillation pressure (p2) is about 5 bar.

19. The method according to claim 12, wherein said solution is at least partially evaporated by means of the effect of said heat exchange.

* * * * *